United States Patent
Stöber

(10) Patent No.: US 7,969,565 B2
(45) Date of Patent: Jun. 28, 2011

(54) DEVICE FOR INSPECTING A SURFACE

(75) Inventor: Bernd Rüdiger Stöber, Rheda-Wiedenbrück (DE)

(73) Assignee: Koenig & Bauer Aktiengesellschaft, Wurzburg (DE)

( * ) Notice: Subject to any disclaimer, the term of this patent is extended or adjusted under 35 U.S.C. 154(b) by 518 days.

(21) Appl. No.: 11/922,045

(22) PCT Filed: Jul. 5, 2006

(86) PCT No.: PCT/EP2006/063913
§ 371 (c)(1),
(2), (4) Date: Dec. 12, 2007

(87) PCT Pub. No.: WO2007/006706
PCT Pub. Date: Jan. 18, 2007

(65) Prior Publication Data
US 2009/0109430 A1 Apr. 30, 2009

(30) Foreign Application Priority Data
Jul. 8, 2005 (DE) .......................... 10 2005 031 957

(51) Int. Cl.
| G01N 21/00 | (2006.01) |
| G01N 21/55 | (2006.01) |
| G01N 21/86 | (2006.01) |
| G06K 9/74 | (2006.01) |
| G06K 9/00 | (2006.01) |
| G01B 11/30 | (2006.01) |
| G01V 8/00 | (2006.01) |

(52) U.S. Cl. ....... 356/237.2; 356/71; 356/445; 356/600; 250/559.01; 250/559.04; 250/559.4; 250/559.44; 382/112; 382/135

(58) Field of Classification Search .................. None
See application file for complete search history.

(56) References Cited

U.S. PATENT DOCUMENTS
4,357,596 A * 11/1982 Feilchenfeld ................. 235/436
(Continued)

FOREIGN PATENT DOCUMENTS
DE 35 40 288 C2 1/1987
(Continued)

*Primary Examiner* — Michael P Stafira
*Assistant Examiner* — Gordon J Stock, Jr.
(74) *Attorney, Agent, or Firm* — Jones, Tullar & Cooper, P.C.

(57) ABSTRACT

A device that is usable to inspect the surface of a material uses an inspection system which includes an optical unit. That optical unit can register the light which is reflected by the surface to be inspected. An illumination system, that uses at least two light sources, provides the light. The optical unit and the illumination system are connected to a control unit. The at least two light sources are arranged spaced at a distance from each other and both emit light directed to a recording region of the optical unit. The optical unit is oriented toward the surface to be inspected and at least one of the illumination light sources can be subdivided into several individual light sources. The control unit controls at least two of the illumination system light sources that are arranged at a distance from each other or the respective individual light sources of at least one of the illumination sources both selectively and independently of each other. The recording region of the optical unit lies on a displacement plane of the surface to be inspected with that surface being displaced through the recording region in relation to the inspection system. The distance between the light sources of the illumination system extends in the displacement direction of the surface to be inspected. The individual light sources of at least one of the sources are arranged transversely to the displacement direction of the surface to be inspected.

27 Claims, 3 Drawing Sheets

U.S. PATENT DOCUMENTS

| | | | |
|---|---|---|---|
| 4,592,090 A | | 5/1986 | Curl et al. |
| 4,677,473 A | | 6/1987 | Okamoto et al. |
| 4,685,139 A | * | 8/1987 | Masuda et al. ............... 382/112 |
| 4,750,140 A | * | 6/1988 | Asano et al. ................ 382/108 |
| 4,775,238 A | * | 10/1988 | Weber ........................ 356/431 |
| 4,791,493 A | | 12/1988 | Ogura et al. |
| 5,301,129 A | * | 4/1994 | McKaughan et al. ........ 382/149 |
| 5,304,813 A | | 4/1994 | De Man |
| 5,540,152 A | * | 7/1996 | DeMoore ..................... 101/483 |
| 5,764,251 A | * | 6/1998 | Hashimoto ................... 347/16 |
| 5,936,353 A | | 8/1999 | Triner et al. |
| 6,061,121 A | | 5/2000 | Holl et al. |
| 6,081,608 A | * | 6/2000 | Fujii et al. ................... 382/112 |
| 6,101,266 A | * | 8/2000 | Laskowski et al. ........... 382/135 |
| 6,566,670 B1 | * | 5/2003 | Buisker et al. ............ 250/559.36 |
| 6,774,986 B2 | * | 8/2004 | Laskowski ..................... 356/71 |
| 6,838,687 B2 | * | 1/2005 | Tullis et al. ............. 250/559.07 |
| 6,914,684 B1 | * | 7/2005 | Bolash et al. ................ 356/600 |
| 7,167,247 B2 | * | 1/2007 | Uemura et al. ............... 356/432 |
| 7,171,032 B2 | * | 1/2007 | Jones et al. .................. 382/135 |
| 7,345,747 B2 | * | 3/2008 | Hillmann et al. ............... 356/71 |
| 7,677,379 B2 | * | 3/2010 | Nago et al. ................... 194/207 |
| 7,705,293 B2 | * | 4/2010 | Miyahara et al. ............. 250/239 |
| 7,798,634 B2 | * | 9/2010 | Miyahara et al. ............. 347/106 |
| 7,880,875 B2 | * | 2/2011 | Moddemeyer et al. .... 356/237.2 |
| 2005/0002069 A1 | | 1/2005 | Schnitzlein et al. |
| 2005/0217969 A1 | * | 10/2005 | Coombs et al. ............... 194/206 |
| 2006/0081139 A1 | * | 4/2006 | Bolza-Schunemann ...... 101/148 |
| 2006/0251320 A1 | | 11/2006 | Diederichs et al. |
| 2007/0188722 A1 | | 8/2007 | Stober |

FOREIGN PATENT DOCUMENTS

| | | |
|---|---|---|
| DE | 41 23 916 A1 | 1/1992 |
| DE | 41 23 916 C2 | 1/1992 |
| DE | 195 11 782 C2 | 10/1996 |
| DE | 198 59 512 A1 | 7/2000 |
| DE | 199 30 688 A1 | 1/2001 |
| DE | 100 61 070 A1 | 6/2002 |
| DE | 102 04 939 A1 | 9/2003 |
| DE | 102 34 431 A1 | 2/2004 |
| DE | 102 61 865 A1 | 7/2004 |
| DE | 10 2004 014 541 | 5/2005 |
| EP | 0 537 431 A1 | 4/1993 |
| EP | 0 537 513 A1 | 4/1993 |
| EP | 0 675 466 A2 | 3/1995 |
| WO | WO 01/54077 | 7/2001 |
| WO | WO 2004054804 A1 * | 7/2004 |
| WO | WO 2004/086291 A2 | 10/2004 |

* cited by examiner

DEVICE FOR INSPECTING A SURFACE

CROSS-REFERENCE TO RELATED APPLICATIONS

This application is the U.S. national phase, under 35 USC 371, of PCT/EP2006/063913, filed Jul. 5, 2006; published as WO 2007/006706 A1 on Jan. 18, 2007, and claiming priority to DE 10 2005 031 957.2, filed Jul. 8, 2005, the disclosures of which are expressly incorporated herein by reference.

FIELD OF THE INVENTION

The present invention is directed to a device for inspecting a surface. An inspection system includes an optical unit that registers light which has been reflected from a surface which is to be inspected. An illumination system has at least two light sources. The optical unit and the illumination system are connected to a control unit.

BACKGROUND OF THE INVENTION

DE 102 04 939 A1 relates to a device for generating flat, parallel light. An optical unit, for use in registering the light that is reflected from a surface to be inspected, and an illumination system having at least two light sources, are provided. The optical unit and the illumination system are connected to a control unit. The light sources are arranged at a distance from one another. Each of the light sources emits light in a recording area of the optical unit, which recording area is provided on the surface to be inspected. The optical unit is oriented toward the surface to be inspected. At least one of the light sources of the illumination system, which light sources are arranged at a distance from one another, is subdivided into a plurality of individual light sources. The recording area of the optical unit lies within a plane of motion of the surface to be inspected, which surface is moved through this recording area. The spacing of the light sources of the illumination system extends in the direction of motion of the surface to be inspected. The individual light sources of at least one of these light sources are arranged transversely to the direction of motion of the surface to be inspected.

DE 10 2004 014 541 B3 discloses an optical system for use in generating an illuminated strip on a surface of a material. At least a portion of the surface of the material is reflective. Relative motion between the surface of the material and the illuminated strip is provided. An illumination device, having a plurality of light sources which are arranged side by side in a linear fashion and which are spaced at a distance from the surface of the material, and which emit light respectively at a spatial angle, emit light for generating the illuminated strip. A recording device records light that is reflected from the surface of the material with at least one detector which is positioned at a distance from the surface of the material. The illuminated strip is configured to have a width that extends orthogonally relative to its length on the surface of the material.

DE 199 30 688 A1 discloses a device for inspecting a surface. An inspection system, comprising an optical unit for registering the light which is reflected from the surface to be inspected, and an illumination system having at least two light sources, is provided. The optical unit and the illumination system are connected to a control unit. The light sources are arranged at a distance from one another. Each of the light sources emits light in a recording area for the optical unit, which recording area is provided on the surface to be inspected, with each light source emitting its light at a respective angle of incidence that is different from the others. The optical unit is oriented at a viewing angle toward the surface to be inspected.

DE 41 23 916 A1 discloses a device for use in the illumination-dynamic recognition and classification of surface characteristics of an object. At least one of the light sources of an illumination system, which light sources are arranged at a distance from one another, is sub-divided into a plurality of separate light sources. A control unit adjusts at least two of the light sources of the illumination system, which are arranged at a distance from one another, and/or the individual light sources of at least one of the light sources, which are arranged at a distance from one another, selectively and independently of one another.

The preferred use of the present invention is directed especially to the inspection of surfaces having non-uniform reflective areas. Surfaces of this type, with non-uniform reflective areas, are generally known, for example, in surfaces of a substrate material which is used for print products. Examples of this type of surface include products that are printed in security printing and in package printing processes, and especially in package printing processes for producing high-quality packaging, such as, for example, packaging for perfumes or for other luxury items. Security printing includes the production of, for example, bank notes, postage stamps or of documents, such as legal documents, share certificates, checks, and official identification papers or passes. Printed products having non-uniform reflective surfaces are typically produced, for example, in a special printing process. Such a special printing process can consist of a combination of known printing processes, such as of offset printing, intaglio printing or letterpress printing.

Non-uniform reflective surfaces are formed in these printed products, for example, by equipping the printing substrate with at least one special optical and/or haptic feature, in addition to the actual print motif. The haptic feature generally also has an optical effect. The special feature forms, for example, a security feature that serves to confirm the authenticity of the product and to make falsification of the printed product more difficult. However, the special feature may also be provided to form a particular aesthetic appeal for this printed product. For instance, in addition to the conventional ink that is applied, a special ink, such as, for example, an OVI ink, or optical variable ink, a lacquer, or a foil, can be applied to the surface of this printed product.

A haptic feature, which is one that is discernible by touch, is produced, for example, by providing the surface of the printed product with a relief-like structure. This may be accomplished, for example, through embossing and/or through a change in thickness of the printing substrate, or, for example, by giving the surface of the printed product a perforation, such as a micro-perforation. For example, a water mark, which is incorporated into the printing substrate, can be formed by varying the thickness of the substrate. With surface structures of this type, light that is incident at these points on the surface of the printed product is reflected differently from light that is incident on other areas of the surface of this printed product. Under certain circumstances, such incident light is not reflected at all.

An OVI, or optical variable ink, has the property that its perceived color changes depending upon its viewing angle, with such an ink changing color, for example, from reddish purple to olive green or to brown, due to the fact that incident light is refracted, scattered or reflected on pigments of the OVI ink. Special inks also may include fluorescent inks, for example, which contain pigments that luminesce, for example, in the dark or only with the incidence of light of a certain wavelength, such as a UV light. A similar optical effect may be produced, for example, by mixing mottling fibers into the printing substrate, which fibers luminesce in various colors under the incidence of, for example, UV light.

A lacquer, which may be applied especially to only a portion of the surface of the printed product, creates, for example, a glossy effect, which glossy effect alters the reflectivity of the surface of this printed product significantly as compared with an unlacquered area of the surface of the printed product. A lacquer, such as a transparent lacquer, can reflect incident light like a metallic surface. However, it will substantially decrease the visibility of a print motif disposed underneath the lacquer on the printing substrate, depending upon the angle of incidence of the incident light. A glossy strip, such as a shiny, gold-colored strip, which may be applied, for example, to a bank note as a security feature, also produces a particularly glossy effect.

At least one area on the surface of the printed product can also be configured with a material that is different from the printing substrate. The reflectivity of this different material may be different from that of the printing substrate. Areas of this type are formed, for example, by at least one foil element, such as, for example, by a metal, such as aluminum, or by a plastic, such as polypropylene or some other stable plastic. The foil element, in turn, can have a hologram. A security strip or a security thread can also be an element of this type. Sometimes, a foil element of this type also has a partial microstructure for the purpose of selectively altering its reflective property in a partial area. Obviously, therefore, foil elements can also give the surface of the printed product a non-uniform reflective structure.

Common to all of the embodiments of the special optical feature and/or the special haptic feature mentioned above, by way of example, is that they present a special challenge when one or even when several of these different features are to be inspected at the same time as is the print motif applied to the substrate, with such an inspection being done in order to assess the quality of the printed product. This is because the substrate itself, and the conventional ink printed onto that substrate, to produce the print motif, generally reflect incident light diffusely in a larger solid angle, in other words scattering it, without a pronounced preferred direction. This is typically due to their irregular and therefore rougher surface quality. A metallic or metalized foil element, which may be incorporated into the printing substrate or applied to its surface, or a lacquer that is applied to the surface of the printing substrate, generally reflects incident light in a preferred direction in accordance with the law of reflection, due to its regular and therefore smoother surface property. According to the law of reflection, the reflection angle corresponds to the angle of the incident light, and these two angles, along with the perpendicular of incidence, which is based upon the surface of the printing substrate, lie within the same plane.

An inspection system for use in inspecting the quality of a printed product has, for example, an optical unit which is used for registering the light that has been reflected from the surface to be inspected. This optical unit is preferably an imaging unit, such as, for example, a camera system, and especially a camera system for use in recording a color image. The inspection system also includes an illumination system for illuminating the surface of the printing substrate, or at least for illuminating the non-uniform reflective areas of the surface of this printing substrate. An inspection system of this type is described, for example, in the prior art documents DE 198 59 512A1 or DE 100 61 070A1.

The above-discussed challenge of inspecting a printed product having non-uniform reflective areas on its surface arises because the ability to inspect non-uniform reflective areas is optimal only when an angular position between the camera system and the illumination system is adjusted based upon the reflectivity of the respective surface.

SUMMARY OF THE INVENTION

The object of the present invention is directed to the provision of a device for use in inspecting a surface, and wherein the device is capable of assessing the quality of a surface that is being moved within the recording area of the inspection system and which has areas of different reflectivity.

The object is attained, in accordance with the invention with the provision of an inspection system including an optical unit for use in registering light which is reflected from the surface to be inspected. An illumination system has at least two light sources. These light sources are positioned spaced from each other at a distance. Each of the light sources emits light in a recording area of the optical unit, which recording area is on the surface to be inspected. At least one of the light sources of the illumination system is subdivided into a plurality of individual light sources. The recording area of the optical unit lies within a plane of motion of the surface to be inspected. The individual light sources are positioned transversely to the direction of motion.

The benefits to be achieved with the present invention consist especially in that, when using a single camera system and a single illumination system, printed products having non-uniform reflective surface areas, which printed products are being moved during their inspection, can be reliably and very accurately inspected. The camera system and the illumination system of the inspection system are arranged in a fixed angular position in relation to one another. They remain in this position for the inspection of printing substrates having surfaces with different reflectivity. In the device for inspecting a surface, in accordance with the present invention, no change in the angular position between the camera system and the illumination system is required for the inspection of surfaces having different reflectivity. The inspection system of the present invention can be adapted for inspecting surfaces having different reflectivity, without any mechanical adjustment, such as, for example, without a change in the angular position between the camera system and the illumination system implemented via a mechanical adjustment. This can be done solely by adjusting the preferably electronic control of the illumination system.

This independence of the angular position between the camera system and the illumination system, which is obtained through the control of the illumination system, provides advantages when the inspection system, in accordance with the present invention, is used in a printing press, and especially for performing an inline inspection. The quality of printed products, which are produced in the printing press, is assessed in real time during the production process. The printed products are inspected as they are moved in relation to the inspection system. Such relative movement generally consists in that, during its inspection, the printed substrate is moved at high speed through a recording area of the camera system of the inspection system, which camera system is stationarily positioned in the printing press. The inspection of the entire printed substrate, with all of its differently reflective surface areas, can be accomplished with the solution, in accordance with the present invention, without requiring various adjustment processes in the printing press that would impair the production process, or in other words, without adjustments to mechanical equipment. The provision of different illumination situations, which are necessary for the intended inspection of a certain sample, is shifted to the plane of the preferably electronic, program-supported control of the inspection system. The inspection system thus becomes easily adaptable to the intended sample.

BRIEF DESCRIPTION OF THE DRAWINGS

One preferred embodiment of a device for inspecting a surface, in accordance with the present invention is represented in the set of drawings and will be described in greater detail in what follows, wherein additional advantages will be specified.

The drawings show in.

DESCRIPTION OF THE PREFERRED EMBODIMENTS

Figure 1:
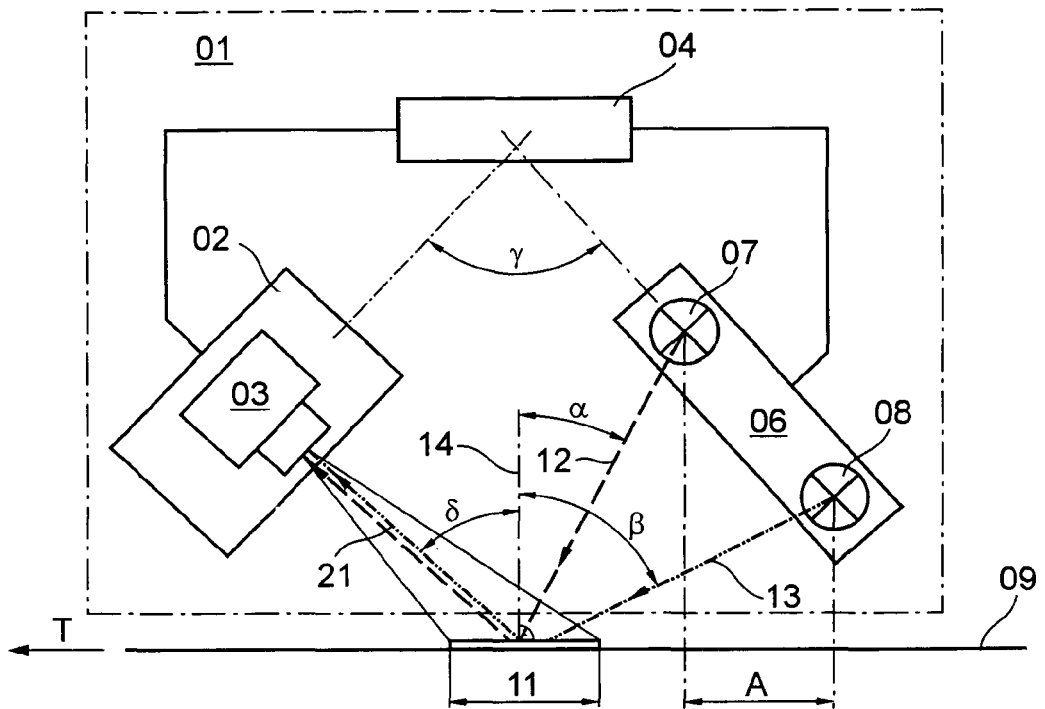
FIG. 1 a schematic representation of an inspection system with a camera system having one camera, and with an illumination system having two light sources.

FIG. 1 is a schematic representation of the principle of an inspection system 01 in accordance with the present invention, and with an optical unit 02 for registering the light which has been reflected from a surface to be inspected, and with an illumination system 06 having at least two light sources 07; 08. The optical unit 02 and the illumination system 06 are connected to a control unit 04. The optical unit 02 is preferably configured as a camera system 02 having at least one camera 03.

A surface to be inspected, which is preferably the surface of a printing substrate 09, such as a sheet 09 or a material web 09, and especially a paper web 09, the quality of which surface is to be assessed, is moved, preferably uniformly, through a recording area 11 of the camera 03 of the camera system 02. This recording area 11 lies within a plane of transport of the printing substrate 09 and extends in a direction of motion T, or in the transport direction T. A rate of motion of the surface to be inspected, which in this case, is the rate of transport of the printing substrate 09, can amount to, for example, 18,000 sheets per hour, or in the case of a web-type printing substrate 09, 12 m/s, can amount to even greater respective speeds.

Figure 2:
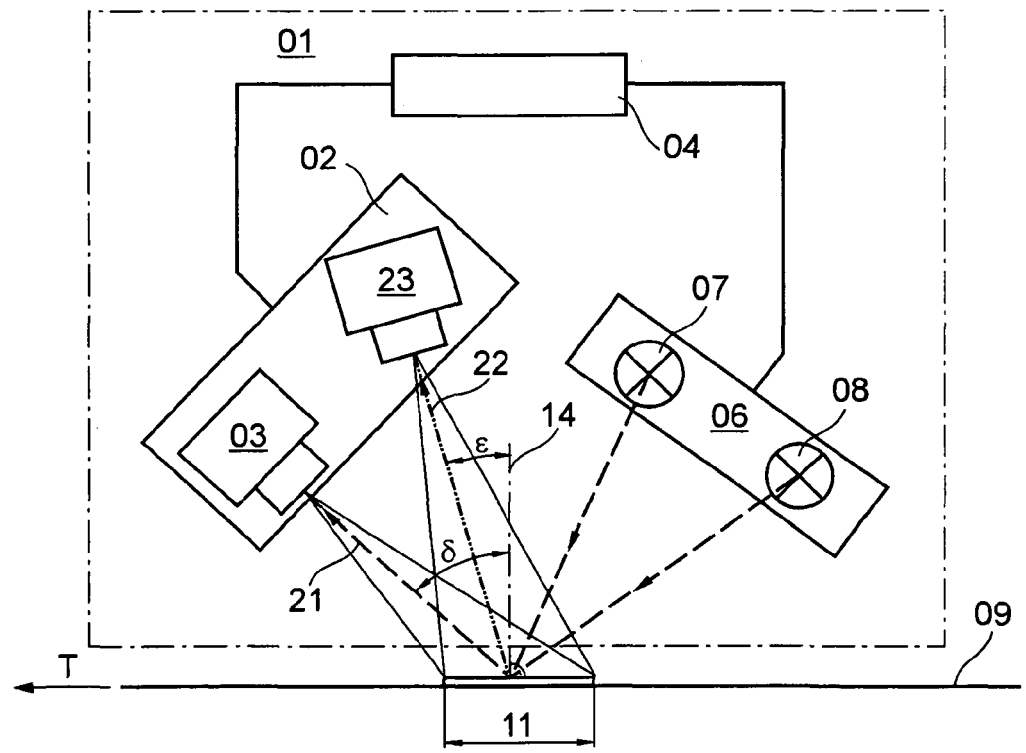
in FIG. 2 a schematic representation of an inspection system with a camera system having two cameras, and with an illumination system having two light sources.

The surface to be inspected, typically the surface of the printing substrate 09, has at least one motif, such as, for example, an applied image motif, and especially a print motif, on at least its side that faces the inspection system 01, and additionally has at least one special feature on that same side. The print motif and the special feature differ from one another in their respective optical effect, and especially vary from each other in their reflectivity, and thus form non-uniform reflective areas on the surface to be inspected. Light is emitted by the light sources 07; 08 of the illumination system 06 and is incident in the recording area 11 of the camera 03 of the camera system 02. This is schematically indicated in FIGS. 1 and 2 by only a respective central beam 12; 13. This light is consequently reflected differently from the different surfaces on the substrate 09 having their non-uniform reflective configurations. For example, the print motif containing printing ink, and the unprinted areas of the printing substrate 09, which are adjacent, for example, to the print motif, reflect light that is emitted by the light sources 07; 08 and which is incident in the recording area 11, diffusely due to their respective surface quality. The at least one additional feature of the substrate 09 reflects the same incident light, for example, in a specular fashion, such as, for example, in a certain preferred direction, due to its surface quality.

The camera 03 of the camera system or optical unit 02 is configured, for example, as a color camera 03, and preferably is configured as a semiconductor camera 03 that has at least one CCD chip. It is specifically configured as a line camera 03, wherein light-sensitive sensors of the line camera 03 are arranged in a linear pattern extended transversely to the direction of transport T of the printing substrate 09. The surface of the printing substrate 09, that is being moved relative to the inspection system 01, is scanned in correlation to its transport speed, advancing line-by-line. When a line camera 03 is used, the complete imaging of a print motif, or of a special feature on the printing substrate 09 generally requires the recording of a multitude of sequentially registered scanning lines, with each scanning line recording a section of the print motif or of the special feature.

The at least two separate light sources 07; 08 of the illumination system 06 are offset by a distance A in relation to one another in the transport direction T of the printing substrate 09 as may be seen in FIG. 1. Light which is emitted by the two light sources 07, 08 is incident in the recording area 11 of the camera 03 of the camera system or optical unit 02 at different angles of incidence $\alpha$; $\beta$, again as seen in FIG. 1. Each of the respective angles of incidence $\alpha$; $\beta$ is measured from a central beam 12; 13, coming from the respective one 07; 08 of the light sources, to a perpendicular of incidence 14 in the recording area 11 that is positioned vertical on the surface to be inspected, or in other words on the printing substrate 09. Because light emitted by the light sources 07; 08 is incident in the recording area 11 of the camera 03 of the camera system or optical unit 02 at different angles of incidence $\alpha$; $\beta$, with each of these light sources 07; 08, different surface areas of the printing substrate 09, and specifically areas that differ in terms of reflectivity, can be illuminated. Preferably, however, at least one of the light sources 07; 08 is arranged at such an angle of incidence $\alpha$; $\beta$ that light emitted by this light source 07; 08 is reflected from the recording area 11 to the camera 03 based upon the condition that "angle of incidence is equal to angle of reflection". Using this light sources 07; 08, especially reflective features of the printing substrate 09 are readily visible, and can therefore be inspected. The camera 03 of the camera system 02 is oriented at a viewing angle $\delta$ toward the surface of the printing substrate 09, as seen in FIG. 1. The viewing angle $\delta$ is measured between a central beam 21 directed from the recording area 11 toward the camera 03, and the perpendicular of incidence 14 that is vertical on the printing substrate 09. The angle of incidence $\alpha$; $\beta$ and/or the viewing angle $\delta$ are each preferably acute, and thus are each preferably smaller than 90°. The inspection system 01 preferably operates in an incident lighting process. The light sources 07; 08 of the illumination system 06, which are positioned spaced from one another by a distance A in the transport direction T of the printing substrate 09, preferably have the same light color, or allow the same light color to be incident in the recording area 11.

The light sources 07; 08 of the illumination system 06 are preferably configured as light-intense light-emitting diodes, or LED's or as laser diodes which emit their light bundled and selectively in a preferred direction oriented toward the recording area 11. Additional optical units, which are not specifically shown, such as lenses and/or mirror units, can support the directional homogeneity of the light emitted by the light sources 07; 08. These additional optical units are preferably integrated into the illumination system 06 for the purpose of achieving a compact overall structure.

The camera system or optical unit 02 and the illumination system 06 are located in the inspection system 01 in a firmly defined arrangement in relation to one another. They preferably are arranged at a fixed angle γ, in relation to one another. The angle γ remains unchanged, at least during an inspection of the printing substrate 09 having the non-uniform reflective surfaces. For example, both the camera system or optical unit 02 and the illumination system 06 are permanently installed in a printing press 16, such as, for example, in a rotary printing press 16, and preferably are permanently installed in a sheet-fed printing press 16.

Figure 3:
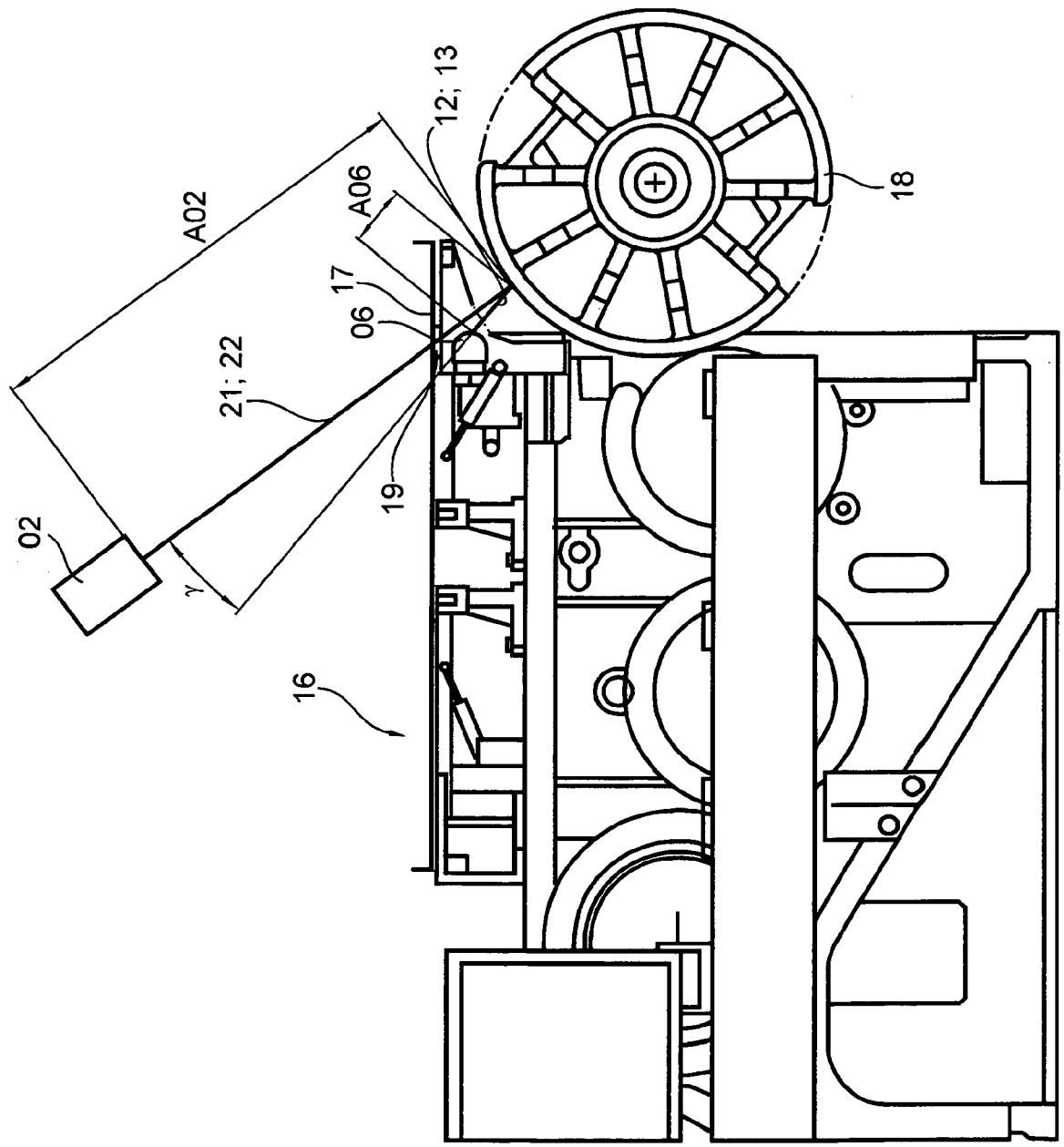
in FIG. 3 a side elevational view of an arrangement of the inspection system of FIG. 1 or 2 in a printing press; and in FIG. 4 a schematic representation of the subdivision of a first light source and of a second light source of the illumination system, each into a plurality of individual light sources.

FIG. 3 shows a side elevation view of a portion of a sheet-fed printing press 16, by way of example, with the inclusion of an inspection system 01 of the type as represented in FIG. 1 and 2. The illumination system 06 is positioned, for example, beneath a pedal mechanism 17. This illumination system 06 emits its light in the direction of a cylinder 18, such as, for example, a printing group cylinder 18, and specifically such as an impression cylinder 18. Light which is reflected from the surface of a printing substrate 09, which is not specifically shown, but that is held on the impression cylinder 18 and that is transported by the rotation of the impression cylinder 18, travels through a gap-type opening 19 in the pedal mechanism 17, and is recorded by a camera system or an optical unit 02 of the inspection system 01. The camera system or optical unit 02 is positioned, for example, at a distance A02, and the illumination system 06 is positioned, for example, at a distance A06, both as depicted in FIG. 3, from the impression cylinder 18. The distance A02 of the camera system 02 from the impression cylinder 18 ranges from 10 mm to 2,000 mm, and preferably ranges from 50 mm to 400 mm. The distance A06 of the illumination system 06 from the impression cylinder 08 preferably ranges from 30 mm to 200 mm, and especially ranges from 80 mm to 140 mm. The distances A02 and A06 are preferably firmly set and are not intended to be altered, at least during an inspection which is to be performed when the printing press 16 is running during a production process. The camera system or optical unit 02 and the illumination system 06 preferably also have a firmly set angle γ in relation to one another.

This angle γ is preferably acute or is approximately a right angle.

The control unit 04, which is depicted in FIGS. 1 and 2, controls at least two light sources 07; 08 of the illumination system 06, which are arranged offset from one another by a distance A in the transport direction T of the printing substrate 09, as seen in FIG. 1, separately from one another, i.e. individually and independently of one another. For example, the control unit 04 adjusts a switch-on time for the light sources 07; 08, the on-period for those light sources, and their respective brightness levels. With light sources 07; 08 having differently adjusted levels of brightness, a contrast between reflective and diffusely reflective features can be selectively adjusted. An adjustment for the respective print order to be processed in the printing press 16 can be implemented. With the selection of a specific light source 07; 08 of the illumination system 06, which light source is arranged at a certain angle of incidence α; β, and with that selection being made via a control accomplished by the control unit 04, the contrast between a feature that is reflective only at a special angular position, and the area surrounding it can be adjusted. This adjustment may be able to be accomplished because, depending upon the reflectivity of the feature, it is more intensely visible either under relatively flat incident side lighting, or at an angle that is close to the perpendicular of incidence 14.

The control unit 04 can control the switch-on time of certain, selected light sources 07; 08, based, for example, upon the transport rate of the printing substrate 09, or upon an angular position of the cylinder 18 transporting the printing substrate 09, and especially based on an angular position of the impression cylinder 18. In either case, for example, the recording area 11 of the camera 03 of the camera system 02 forms a reference point. For example, the light sources 07; 0 may always be switched on by the control unit 04, for example, when a certain angular position of the impression cylinder 18 transporting the printing substrate 09 correlates to the recording area 11 of the camera 03, or, based upon the transport rate of the printing substrate 09, when the printing substrate 09 has traveled defined distances. The selection of the switch-on time of certain selected light sources 07; 08, made by, or via the control unit 04 can, in turn, be dependent, for example, upon the current print order being processed in the printing press 16. This option can be applied to advantage with a print motif or with a special feature that repeats in a rigid sequence, such as, for example, at a fixed distance, such as, for example, one that repeats after each complete or half revolution of the impression cylinder 18 which is transporting the printing substrate 09. The light sources 07; 08 are then preferably again switched off by the control unit 04, once the print motif or the special feature to be recorded has passed entirely through the recording area 11 of the camera 03 of the camera system or optical unit 02, or after the print motif or special feature to be recorded has been recorded in its entirety by the camera 03 of the camera system 02.

By controlling the respective switch-on time and the respective on-period of certain selected light sources 07; 08, the illumination system 06 can be advantageously adjusted to the respective reflectivity of the print motif to be recorded and/or the reflectivity of the special feature to be recorded. Furthermore, the respective switch-on time and the respective on-period of at least one selected light source 07; 08 of the illumination system 06 can be selectively adjusted in relation to a certain print motif or to a special feature to be recorded. This is particularly beneficial wherein this print motif to be recorded or this special feature to be recorded is to be recorded together with other print motifs or with other special features during the same pass of the printing substrate 09 through the recording area 11 of the camera 03 of the camera system or optical unit 02.

Because of the above-described control of the light sources 07; 08 of the illumination system 06, and adjusted to the print motif to be recorded or the special feature to be recorded, OVI inks can also be made recognizable to a camera 03 of the camera system or optical unit 02. Under various illumination situations, which differ especially in terms of the angle of incidence α; β, of the respective light sources 07; 08, a color change can be induced in OVI inks, which color change can be detected by the inspection system 01.

In one preferred embodiment of the inspection system 01 in accordance with the present invention, in which the camera 03 of its camera system or optical unit 02 is configured as a line camera 03, the inspection system 01 can be provided such that the control unit 04 switches the light sources 07; 08 of the illumination system 06 between two sequential scanning lines that are recorded by the line camera 03. In this case, the switching times for the light sources 07; 08 of the illumination system 06 are far below the line cycle for the line camera 03. For example, if two different illumination situations are to be adjusted in the recording area 11 of the camera 03 of the camera system or optical unit 02, such as, for example, by using two light sources 07; 08 of the illumination system 06 that differ in terms of their respective angles of incidence α; β, these light sources 07; 08 must be switched on and off again, in succession, before the printing substrate 09 has traveled a certain distance in its direction of transport T. The extent of this certain distance is based upon the rate of transport of the printing substrate 09, with that distance corresponding to half the length of the recording area 11 in the transport direction T of the printing substrate 09. In this example, it is assumed that one scanning line of the line camera 03 completely records the recording area 11 in its extension that is oriented in the direction of transport T of the printing substrate 09. If a section of the printing substrate 09, that corresponds to half the length of the recording area 11, is to be recorded under the two different illumination situations of the line camera 03, the line camera 03 must have a line cycle that will allow it to read out a scanning line that corresponds to the length of the recording area 11 twice, specifically once after the printing substrate 09 has traveled the distance in its direction of transport T, based upon its rate of transport, that corresponds to half the length of the recording area 11 in the direction of transport T of the printing substrate 09. If more than two partial images are to be recorded under different illumination situations, as the printing substrate 09 passes through the recording area 11, a plurality of light sources 07; 08 of the illumination system 06, with the number of light sources corresponding to the number of partial images to be recorded, must also be adjusted by the control unit 04, at least in terms of their respective switch-on times and their respective on-periods, wherein the light from these plurality of light sources 07; 08 is incident in the recording area 11 at respectively different angles of incidence α; β, and further wherein the line cycle of the line camera 03 is also increased according to the number of partial images to be recorded. Obviously, considering the preferred high rate of transport for the printing substrate 09, and in order to implement this function, light sources 07; 08 that can be switched very rapidly and a line camera 03 having a high line cycle are required for the illumination system 06. The control unit 04 then evaluates the respective partial images, which have been recorded by the line camera 03 in its recording area 11 under different illumination situations, with regard to the respective reflectivity of different features of the printed product. The line height, which is imaged optically by the line camera 03 corresponds, in each case, for example, to the distance traveled by the printing substrate 09 between the at least two line cycles of the line camera 03. The result is that at least two continuous images of the surface of the printing substrate 09, that are displaced in relation to one another, can be extracted from the sequential scanning lines by an alternating allocation.

To facilitate the inspection of highly complex printed products, the number of features that can be accurately inspected can be increased by increasing the number of light sources 07; 08 in the illumination system 06, and also by supplementing the inspection system 01 by at least one additional viewing angle δ; ε, and thereby by at least one additional camera 23, as is illustrated in FIG. 2. In FIG. 2, a schematic representation of an inspection system 01 is shown, by way of example, and which is provided with a camera system 02 having two cameras 03; 23, and with an illumination system 06 having two light sources 07; 08. One camera 03 has the viewing angle 6 and the second, other camera 23, which may be, for example, also a line camera 23 or a color line camera 23, has a viewing angle ε, which is measured between a central beam 22 that is oriented from the recording area 11 to this second camera 23 and the perpendicular of incidence 14 which is oriented vertically on the printing substrate 09, and wherein the two viewing angles δ; ε are different from one another. The two cameras 03; 23 each have a recording area 11 that lies within the plane of motion of the surface to be inspected, and thus which lies within the transport plane of the printing substrate 09, and which extends in its direction of motion T or its transport direction T. These two recording areas are preferably the same area 11, which is indicated in FIG. 2 by lines on both sides of the respective central beam 21; 22. Furthermore, the inspection system 01 represented in FIG. 2 can also have all the features of the inspection system 01 which has previously been specified in connection with FIG. 1.

A further variation of the preferred embodiment of the illumination system 06, in accordance with the present invention, provides for the subdivision of one or more of the light sources 07; 08, which are shown, by way of example, in FIG. 1 and 2, transversely to the direction of motion T of the surface to be inspected, or to the transport direction T of the printing substrate 09. The light sources are preferably divided into a respective plurality of light sources 071 through 077 and/or 081 through 087, which plurality of subdivided light sources can be controlled, for example individually, by the control unit 04. With this arrangement of the light sources 071 through 077 and/or 081 through 087, the control unit 04 can also adjust a light profile transversely to the transport direction T of the printing substrate 09.

Figure 4:
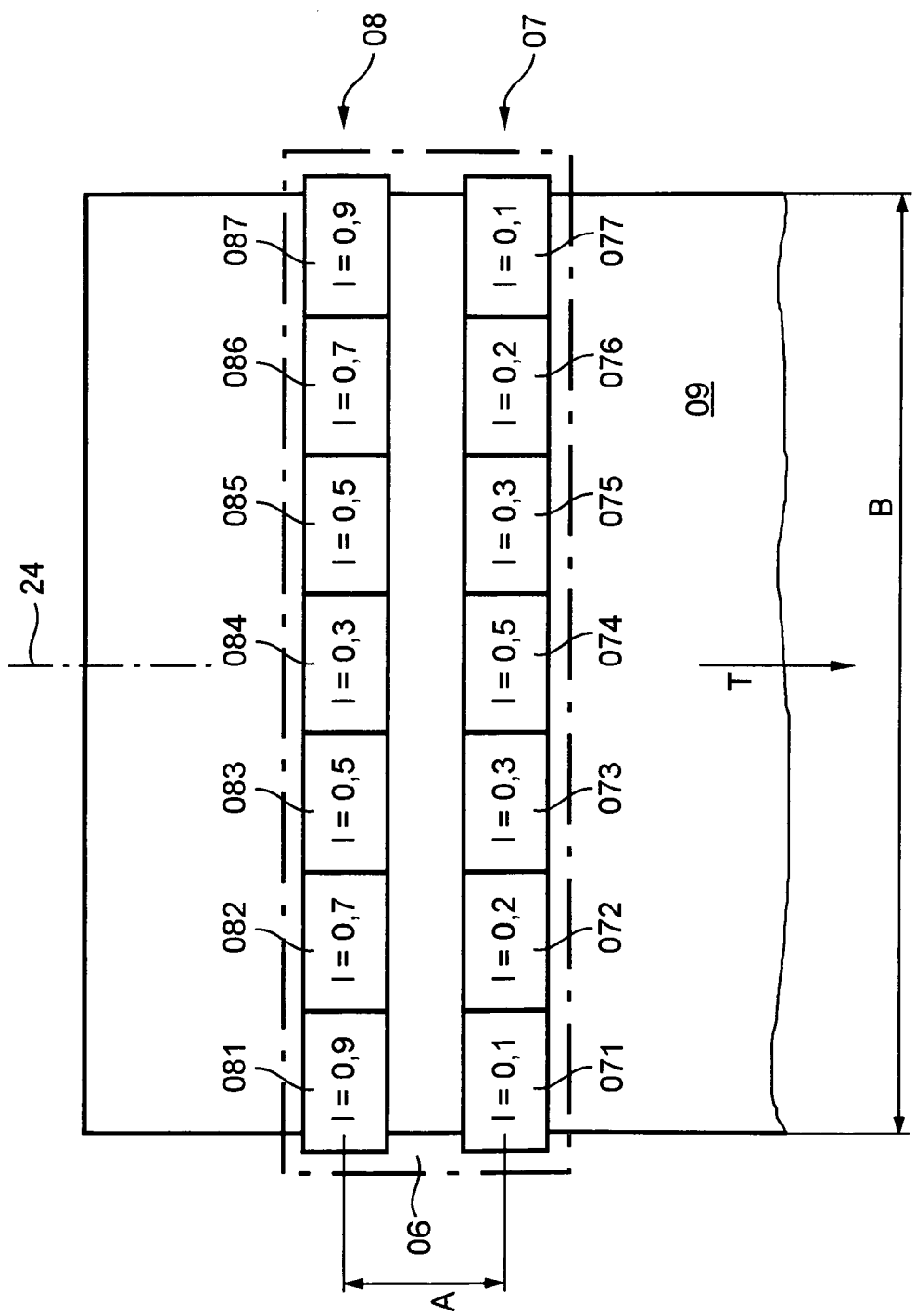

FIG. 4 shows, by way of example, a schematic representation of a plan view of a subdivision of the first light source 07 of the illumination system 06 into a plurality, such as, for example, into seven, individually controllable light sources 071 through 077, arranged in a row. FIG. 4 also shows, a schematic representation of a subdivision of the other, second light source 08 of the illumination system 06 into a plurality, also, for example, seven, individually controllable light sources 081 through 087, which are also arranged in a row. Light, which is emitted by these rows of light sources 07; 08, spaced from one another by the distance A in the transport direction T of the printing substrate 09, is incident, in each case, at respective different angles of incidence α; β in the recording area 11 of the camera 03 of the camera system 02 on the surface of the printing substrate 09. As may be seen in FIG. 4 individual light sources 071 through 077 and/or 081 through 087, each of which is allocated to one of the light sources 07; 08, are arranged transversely to the transport direction T of the printing substrate 09, and thus extend along or across its width B.

The light sources 071 through 077 and/or 081 through 087 are preferably both arranged in separate rows to each form a separate linear illumination unit 07; 08. Each of these separate linear illumination units 07; 08 preferably extends over the entire width B of the printing substrate 09 and even beyond it, all as depicted in FIG. 4. The individual light sources 071 through 077 and/or 081 through 087 of each of the respective linear illumination units 07; 08 are preferably arranged symmetrically, in relation to a line of symmetry 24 that passes through the printing substrate 09 in its transport direction T. Preferably, the same number of individual light sources 071 through 077 and/or 081 through 087 are arranged on both sides of the line of symmetry 24. The linear illumination units 07; 08 can also have differing numbers of individual light sources 071 through 077 and/or 081 through 087 transversely to the transport direction T of the printing substrate 09. Based upon the light that is emitted in the recording area 11, at different angles of incidence α; β, one of the linear illumination units 07; 08 can preferably emphasize reflective features on surfaces of the printing substrate 09 to be illuminated, whereas the other linear illumination unit 07; 08 may be more suited, for example, to illuminating more matte, diffusely reflective features on the surface of the printing substrate 09.

Each of the individual light sources 071 through 077 and/or 081 through 087 can be configured, such as, for example, as a single, light-intense light-emitting diode (LED) or as a laser diode, or as a group containing a plurality of such units. Each of the individual light sources 071 through 077 and/or 081 through 087 is preferably continuously adjustable, for example in terms of its respective brightness level, by the control unit 04. An intensity "I", for example a current level, a voltage level or a timing relationship to the operation of the light sources 071 through 077 and/or 081 through 087, which intensity "I" corresponds to the brightness level of the individual light sources 071 through 077 and/or 081 through 087, can be adjusted, for example, to a value between 0 and 1. The intensity "I" corresponding to zero is for no intensity "I", in other words, the light sources 071 through 077 and/or 081 through 087 are switched off and no light is emitted. An intensity "I" corresponding to one is for full, or for one-hundred percent, maximum intensity "I". Each of the individual light sources 071 through 077 and/or 081 through 087 can preferably be adjusted separately in its intensity "I" by the control unit 04. Adjusted values for the intensity "I" of each of the individual light sources 071 through 077 and/or 081 through 087 of the linear illumination units 07; 08 are shown, by way of example, in FIG. 4 for a particular inspection configuration.

To avoid a large number of control lines extending between the control unit 04 and the light sources 07; 08 of the illumination system 06, it is advantageous to form groups among the individual light sources 071 through 077 and/or 081 through 087 and to control all of the individual light sources 071 through 077 and/or 081 through 087 that belong to one of these groups together using the same control line. FIG. 4 shows an example of an inspection configuration in which individual light sources 071 through 077 and/or 081 through 087, which are arranged symmetrically on both sides of the line of symmetry 24 passing through the printing substrate 09, are each adjusted to the same intensity I, and are preferably controlled together.

The cameras 03; 23 that are part of the camera system or of the optical unit 02 of the inspection system 01 preferably each have a lens system that images the inspected printing substrate 09, for example a lens system, wherein an optical axis of this respective lens system lies, for example, within a plane that intersects the printing substrate 09 orthogonally in its line of symmetry 24. The respective optical axis of the respective lens system preferably corresponds to the respective central beam 21; 22 of the respective camera 03; 23, as is depicted in FIG. 2. Individual light sources 071 through 077 and/or 081 through 087 can preferably also be grouped symmetrically, in relation to the respective optical axis of the respective lens system of the specific camera 03; 23 that records light emitted by these grouped individual light sources 071 through 077 and/or 081 through 087.

A variation of the control of the individual light sources 071 through 077 and/or 081 through 087 can provide for linear illumination units 07; 08 that are part of the illumination system 06 that are able to be adjusted, highly individually, to the reflectivity of the surfaces of the printing substrate 09 to be illuminated and/or in response to other details of the inspection system 01. The result is that even asymmetrical illumination situations can be established.

Depending upon the reflectivity of the surface to be illuminated, and especially upon the reflectivity of the surface of the printing substrate 09, and/or upon certain details of the inspection system 01, either an edge-focused or a center-focused adjustment, in relation to the surface to be inspected, can be advantageous, as depicted in FIG. 4. An edge-focused adjustment can be advantageous, for example, if a wide-angle lens, with physically unavoidable edge fall-off, is used as the imaging lens system in at least one of the cameras 03; 23, and/or if at least one of the linear illumination units 07; 08 has an angle-dependent intensity curve to its respective light outlet.

As a result, with the light sources 07; 08 of the illumination system 06 that can be controlled by the control unit 04, an illumination profile, that can be adjusted, as needed, in response to the respective reflectivity of the surface of the printing substrate 09 to be inspected, without mechanical adjustments to the inspection system 01, can be adjusted preferably both in the transport direction T of the printing substrate 09 and transversely to this transport direction. The control unit 04 can also switch the light sources 07; 08 of the illumination system 06, for example, between two sequential scanning lines which are recorded by the respective line camera 03; 23, in order to record partial images, each under different illumination situations, as the printing substrate 09 passes through the recording area 11 of the camera 03; 23. Surface areas of the printing substrate 09, having very different reflective properties, can be prepared for inspection. The partial images that have been recorded by the camera system 02, under various illumination situations, can together fully image the surface of the printing substrate 09.

With the adjustability of the light sources 07; 08 of the illumination system 06, a more even signal level, with respect to the reflected light, can be adjusted over the entire width of the image, which image width can extend to the width B of the printing substrate 09. The result is that a useful signal/noise ratio is improved in the cameras 03; 23, as is a signal distance between features having different reflective properties. Therefore, in the imaging which is performed with the inspection system 01, images having a more even image property can be generated, which images form an improved basis for assessing the quality of the printed product.

While preferred embodiments of a device for inspecting a surface, in accordance with the present invention, have been set forth fully and completely hereinabove, it will be apparent to one of skill in the art that various changes in, for example, the specific structure of the printing unit, the source of power for the light sources, and the like could be made without departing from the true spirit and scope of the present invention which is accordingly to be limited only by the appended claims.

What is claimed is:

1. A device for inspecting a surface of a printing substrate to be inspected comprising:
   an optical unit adapted to register light reflected from a motif recorded on said surface of said printing substrate to be inspected, said motif recorded on said surface of said printing substrate to be inspected having at least first and second areas of relative reflectivity which are different from each other, said optical unit being oriented toward said surface of said printing substrate to be inspected and defining a recording area of said surface of said printing substrate to be inspected, said printing substrate to be inspected being movable, with respect to said optical unit; at a rate of travel, in a plane of travel. and in a direction of travel in said plane of travel, said recording area of said printing substrate having a width transverse to said direction of travel and a length in said direction of travel;

an illumination system including at least first and second spaced light sources, said first and second spaced light sources being spaced from each other in said illumination system in said direction of travel of said surface of said printing substrate to be inspected, each of said first and second spaced light sources extending over said width of said recording area of said printing substrate, said first spaced light source being adapted to send a first central light beam onto said recording area of said surface of said printing substrate to be inspected at a first angle of incidence, said second spaced light source being adapted to send a second central light beam onto said recording area of said surface of said printing substrate to be inspected at a second angle of incidence different from said first angle of incidence, said illumination system forming a two-dimensional illumination profile having adjustable light intensity values during on-periods of said illumination system on said surface of said printing substrate to be inspected, both in said direction of travel, and transverse to said direction of travel of said surface of said printing substrate to be inspected;

a plurality of individual lights in at least one of said first and second spaced light sources, said plurality of individual lights in said at least one of said first and second spaced light sources extending over said width of said recording area of said printing substrate to be inspected and being spaced transversely from each other to said direction of travel of said surface of said printing substrate to be inspected; and a control unit controlling said at least first and second spaced light sources of said illumination system and controlling said plurality of individual lights in said at least one of said at least first and second spaced light sources selectively and independently of each other in accordance with said at least first and second areas of different relative reflectivity of said surface of said printing substrate to be inspected, said control unit controlling switch-on times of said at least first and second spaced light sources of said illumination system in response to said rate of travel of said printing substrate through said recording area and also selectively controlling said switch-on times, on-periods and brightness levels of each of said at least first and second spaced light sources to adjust said two-dimensional illumination profile illuminating said recording area in response to said motif recorded on said surface of said printing substrate to be inspected and providing different illumination situations for said surface of said printing substrate to be inspected in accordance with said differences in said relative reflectivities of said motif recorded on said surface of said printing substrate to be inspected, said light intensity values of said two-dimensional illumination profile in said recording area being adjusted by said control unit in both said direction of travel and transverse to said direction of travel of said surface of said printing substrate to be inspected in response to said different areas of relative reflectivity of said motif recorded on said surface of said printing substrate to be inspected, as said surface of said printing substrate to be inspected travels through said recording area, said optical unit, said illumination system and said control unit defining an inspection system for said at least first and second areas of respective reflectivity difference of said motif recorded on said surface of said printing substrate to be inspected.

2. The device of claim 1 wherein both of said first and second central light beam angles of incidence are acute angles when measured with respect to a perpendicular of incidence that is vertical on said surface of said printing substrate to be inspected.

3. The device of claim 1 wherein said control unit adjusts at least two different illumination situations in said recording area using said at least first and second spaced light sources having said first and second central light beam angles of incidence different from each other.

4. The device of claim 1 wherein said at least first and second spaced light sources of said illumination system are one of light-emitting devices and laser diodes.

5. The device of claim 1 wherein said control unit is adapted to switch said at least first and second spaced light sources on and off in sequence before said surface of said printing substrate to be inspected can travel a distance in said direction of travel that corresponds to one half of said recording area in said direction of travel.

6. The device of claim 1 wherein selected ones of said plurality of individual lights in said at least one of said first and second spaced light sources are combinable in a fight group and further wherein said control unit is adapted to control said light group.

7. The device of claim 1 wherein said plurality of individual lights are controllable individually by said control unit.

8. The device of claim 1 wherein said plurality of individual lights are arranged in rows to form a linear said at least first and second spaced light sources.

9. The device of claim 1 wherein said control unit is adapted to adjust said plurality of individual lights to form one of an edge-focused and a center-focused light profile in relation to said surface of said panting substrate to be inspected.

10. The device of claim 1 wherein said printing substrate to be inspected is a plurality of individual sheets, said plurality of individual sheets being movable through said recording area of said optical unit at a transport rate of 18,000 sheets per hour.

11. The device of claim 1 wherein said printing substrate to be inspected is a running web which is movable through said recording area of said optical unit at a transport rate of at least 12 m/s.

12. The device of claim 1 wherein said printing substrate to be inspected includes non-reflective areas.

13. The device of claim 1 wherein said at least first and second spaced light sources are arranged transversely to said direction of travel of said printing substrate to be inspected.

14. The device of claim 1 wherein said plurality of individual lights in at least one of said first and second spaced light sources are arranged transversely to said direction of travel of said printing substrate to be inspected.

15. The device of claim 1 wherein said optical unit is oriented toward said surface of said printing substrate to be inspected at a viewing angle.

16. The device of claim 1 wherein said at least first and second spaced light sources are symmetrical about a line of symmetry passing through said printing substrate to be inspected in said direction of travel.

17. The device of claim 1 further including a printing press, said device being arranged in said printing press.

18. The device of claim 1 wherein said optical unit is a camera system and including at least one camera.

19. The device of claim 15 wherein said viewing angle of said optical unit is an acute angle when measured with respect to a perpendicular of incidence that is vertical on said surface of said printing substrate to be inspected.

20. The device of claim 16 wherein said control unit is adapted to adjust said plurality of individual lights arranged symmetrically on both sides of said line of symmetry to the same intensity level.

21. The device of claim 17 further including a cylinder in said printing press and wherein said control unit adjusts a switched-on time of said at least first and second spaced light sources based on an angular position of said cylinder.

22. The device of claim 18 wherein said control unit is adapted to evaluate images recorded by said at least one camera in said recording area under different illumination situations with regard to features of said surface of said printing substrate to be inspected that differ in terms of said relative reflectivities.

23. The device of claim 18 wherein said camera system includes at least first and second cameras with first and second viewing angles different from each other.

24. The device of claim 18 wherein said at least one camera is a line camera.

25. The device of claim 23 wherein said control unit is adapted to align said at least first and second spaced light sources of said illumination system with said at least first and second cameras.

26. The device of claim 24 wherein said at least one line camera has a line cycle and further wherein said at least first and second spaced light sources have switching times shorter than said line cycle.

27. The device of claim 24 wherein said at least one line camera has a line cycle having a cycle time usable to read one scanning line, which corresponds to a length of said recording area, at least twice during passage of a section of said surface of said printing substrate to be inspected by said camera to pass through said recording area.

* * * * *